United States Patent [19]

Picker et al.

[11] Patent Number: 4,851,403

[45] Date of Patent: Jul. 25, 1989

[54] RADIATION SENSITIZERS

[75] Inventors: Donald H. Picker, Merion; Michael J. Abrams, Glenmore; Jean F. Vollano; Christen M. Giandomenico, both of Exton, all of Pa.

[73] Assignee: Johnson Matthey, Inc., Malvern, Pa.

[21] Appl. No.: 41,003

[22] Filed: Apr. 21, 1987

[51] Int. Cl.$^4$ ............................................ A61K 31/555
[52] U.S. Cl. .................................................... 514/185
[58] Field of Search ............... 514/184, 185, 188, 501; 424/1.1

[56] References Cited

U.S. PATENT DOCUMENTS 4,727,068  2/1988  Abrams et al. ...................... 514/185

OTHER PUBLICATIONS

Biochemistry 1983, 22, 2406-2414.
Inorganico Chimica Acta Letters, 104 (1985) L25-27.
Journal of the American Chemical Society, (95:7) Apr., 1973.

Primary Examiner—Douglas W. Robinson
Assistant Examiner—Roger Gobrogge
Attorney, Agent, or Firm—Cushman, Darby & Cushman

[57] ABSTRACT

The present invention relates to a method of potentiating radiation therapy using Co(III) complexes of water soluble, synthetic meso-substituted porphyrins. The method results in the sensitization of both well oxygenated (oxic) and oxygen deficient (hypoxic) tumor cells.

3 Claims, 1 Drawing Sheet

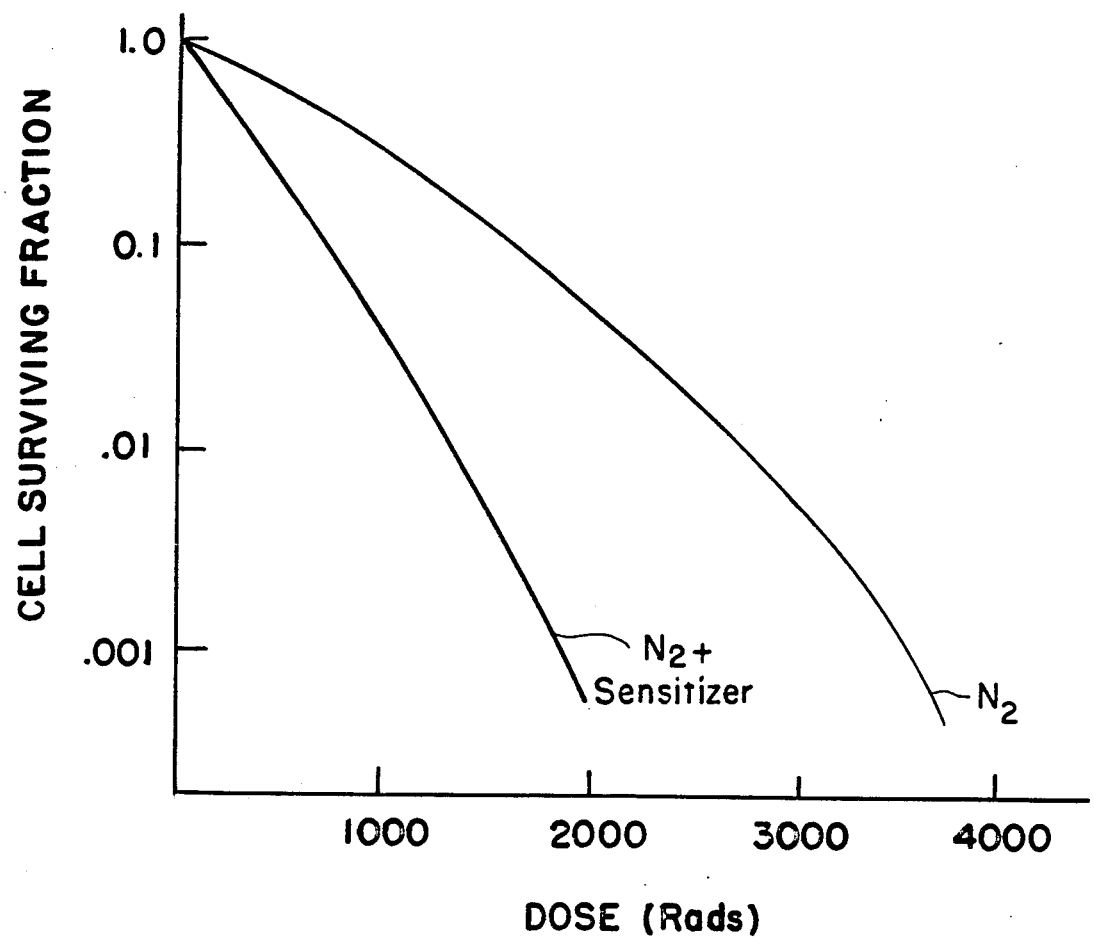

RADIATION SENSITIZERS

BACKGROUND OF THE INVENTION

1. Technical Field

The present invention relates, in general, to radiosensitization and, in particular, to a method of potentiating radiation therapy using Co(III) complexes of water soluble, synthetic porphyrins.

2. Background Information

The use of porphyrin derivatives in combination with visible light as a treatment for cancer is well established. The rationale behind this treatment is that certain porphyrins accumulate in neoplastic tissue; when these porphyrins are exposed to visible light, highly reactive chemical species are formed that destroy the tumor.

One drawback to this "photodynamic therapy" is that deep seated tumors in internal organs are difficult to irradiate with visible light. This problem can be overcome, however, by the use of ionizing radiation, which penetrates tissues more readily than visible light, in conjunction with porphyrins that potentiate the effects of ionizing radiation on tumors.

Several attempts have been made to use porphyrins and metalloporphyrins as radiosensitizers. Hematoporphyrin has been shown to potentiate the effectiveness of X-rays in treating rhabdomyosarcoma in mice. While little or no beneficial effect has been seen in human patients administered hematoporphyrin, metal complexes of meso-tetra(p-carboxyphenyl)porphine (particularly the Zn and Ni complexes) have been found to be radiosensitizers of human tumor cells in vitro.

Most of the radiosensitizers described in the literature sensitize only hypoxic (oxygen deficient) cells. Since some tumors are thought to have regions of hypoxic tissue which are insensitive to the effects of ionizing radiation, these radiosensitizers are therapeutically beneficial because they potentiate the radiation killing of hypoxic cells but do not sensitize normal tissue which is well oxygenated. These compounds, however, are not useful in sensitizing oxic (well oxygenated) tumor cells.

SUMMARY OF THE INVENTION

It is a general object of the invention to obviate or minimize the objections to prior art radiosensitizers.

It is a particular object of the invention to provide a method for sensitizing both oxic and hypoxic cancer cells to ionizing radiation.

Further objects and advantages of the present invention will be apparent from the following detailed description of the species thereof.

The foregoing objects of the invention are achieved by the administration, together with a pharmaceutically acceptable carrier, of Co (III) complexes of water soluble, synthetic meso-substituted porphyrins of the general formula (I):

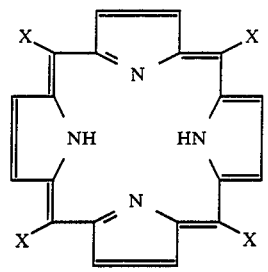

where X=

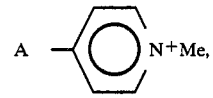

or the corresponding compound with the N in the 2 or 3 position;

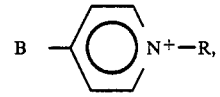

or the corresponding compound with the N in the 2 or 3 position, where R=a $C_2$-$C_6$ n-alkyl, advantageously, R=n-$C_4H_9$;

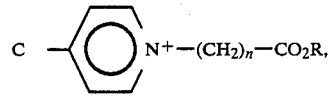

or the corresponding compound with the N in the 2 or 3 position, where n=1-4 and R=methyl, ethyl, or hydrogen;

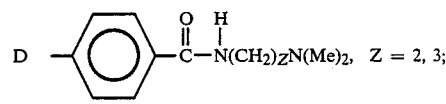

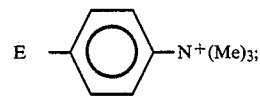

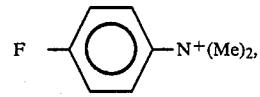

where R=$C_3$-$C_6$ n-alkyl;

-continued

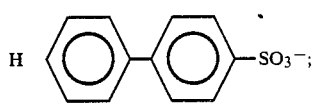

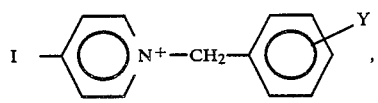

where Y=H, Cl, Br, or NO₂; or

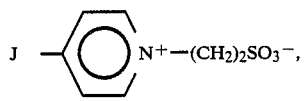

or the corresponding compound with the N in the 2 or 3 position.

These compounds accumulate in cancer cells and interact with ionizing radiation administered to those cells, thereby increasing cell kill during cancer treatment. These cobalt complexes of porphyrins sensitize both oxic and hypoxic cells.

BRIEF DESCRIPTION OF THE DRAWING

FIGURE: Survival Curves

DESCRIPTION OF THE PREFERRED EMBODIMENT

The invention contemplates the use as radiosensitizing agents of compounds having the formula (I):

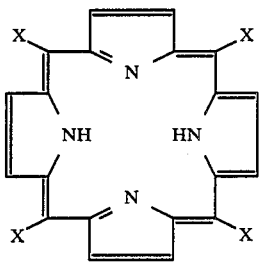

where X=

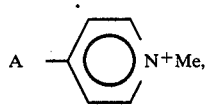

or the corresponding compound with the N in the 2 or 3 position;

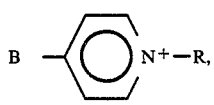

or the corresponding compound with the N in the 2 or 3 position, where R=a $C_2$-$C_6$ n-alkyl, advantageously, R=

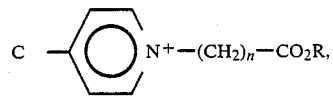

n-$C_4H_9$; or the corresponding compound with the N in the 2 or 3 position, where n=1-4 and R=methyl, ethyl or hydrogen;

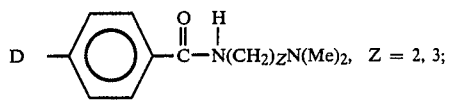

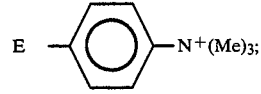

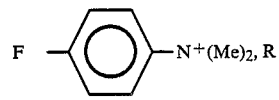

where R=$C_3$-$C_6$ n-alkyl;

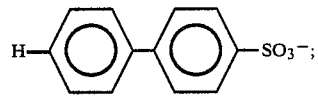

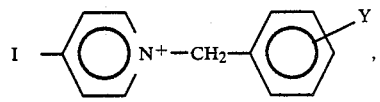

where Y=H, Cl, Br, or NO₂; or

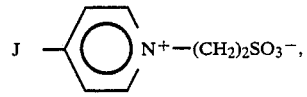

or the corresponding compound with the N in the 2 or 3 position.

Compounds A, E and G above are known and their preparation is shown in the chemical literature. The remaining compounds are new, however, they can be prepared using known methods.

When X is a cation, the compound will have a net charge of +5 and will have associated with it counterions which may be selected from Cl⁻, Br⁻, I⁻, $BF_4^-$, tosylate⁻, $SO_4^{--}$, or the like. When X is an anion, the compound will have a net charge of −3 and will have associated with it counterions which may be selected from H⁺, Na⁺, K⁺, $NH_4^+$, or the like.

The metalloporphyrins of formula (I) exhibit increased accumulation in tumors (Wang et al, *Radiopharmaceuticals, Structure-Activity Relationships,* Richard P. Spenser Ed., 225-249, 1981) and thus have unique sensitizing properties in that they sensitize both hypoxic and oxic cells.

The invention contemplates not only the use of the above-noted compounds for use as radiosensitizers but, in addition, pharmaceutical compositions for such use which include the indicated compounds as the effective radiosensitizing agent, together with a pharmaceutically-acceptable solid or liquid carrier, diluent or excipient therefor. These compositions may take any of the conventional forms for effective administration, e.g. pills, tablets, sterile injection solutios and the like, containing an effective amount of one or more of the compounds of formula (I). The radiosensitizers may be administered, advantageously, in a concentration of from 5-30 mg/ml.

The indicated composition may be used in a conventional manner for radiosensitizing purposes in combination with irradiation or the like in the treatment of cancer. Preferably the compound is administered before irradiation in the usual amounts to effect radiosensitization although the administration may also occur concurrently with the irradiation.

Radiosensitizers for use according to the invention may be evaluated in toxicity and radiosensitization screens. Advantageous methods of testing are as follows:

The compounds are dissolved in Hank's Balanced Salt Solution (HBSS) in concentrations of 500, 200, 100 and 10 $\mu$M. Drug-induced cytotoxicity is tested using 2 petri dishes per concentration (200 cells/dish) in pre-plated, log-phase Chinese hamster V-79 cells. A concentration of, advantageously, 100 mM is used for radiosensitization studies. Otherwise, the concentration selected is the maximum allowed with toxicity less than about 50% (surviving fraction=0.5).

Chinese hamster V-79 cells are grown in 60 mm-diameter plastic or glass dishes containing basal medium (Eagle) with HBSS supplemented with 1% penicillin-streptomycin and Hyclone fetal calf serum. The cells are treated on day 6 as unfed, confluent plateau-phase monolayers. Fresh solutions of the compounds to be tested are prepared in HBSS and added to the cells. Irradiation is performed two hours after administration of the drug using a G.E. Maxitron 300 X-ray machine. Plastic dishes are used for aerated cells while glass dishes are used for hypoxic cells. Induction of hypoxia is initiated immediately following administration of the drug and consists of placing the glass dishes containing cells into aluminum chambers, followed by vacuum pump degassing and purging with nitrogen. The monolayers are trypsinized immediately following irradiation, cell survival is assayed by conventional plating by serial dilution, and colonies are counted 8 days following plating.

By plotting the surviving fraction of cells at a variety of radiation doses, a survival curve can be generated (for example, see FIG. 1).

SER (sensitizer enhancement ratio) is defined as the ratio of radiation doses in the absence and in the presence of the drug which produce the same biological effect. The higher the SER the more effective the sensitizer. An SER of 1.0 indicates no activity.

EXAMPLE 1

Preparation of [Co(tetra-(trimethylaminophenyl)porphine)] [BF$_4$]$_5$ or Co(TMAP) (W. Szulbinski, M. Lapkowski, *Inorg. Chim. Acta.*, 123, 127-133, 1986).

Two hundred and fifty milligrams of [tetra(trimethylaminophenyl)porphine] [tosylate]$_4$ (Strem Chemicals) were dissolved in water (50 ml) and 24 g of CoCl$_2$.6H$_2$O were added. The mixture was refluxed overnight. The mixture was cooled to room temperature and excess of NH$_4$PF$_6$ was added to precipitate a red-violet solid. This material was treated with anion exchange resin (Dowex 2-X8) in the chloride form and the resulting solution of Co(TMAP)(Cl$_5$) was freeze-dried to yield 0.39 g of solid. This material was dissolved in water and treated with a 20% Zn(BF$_4$)$_2$ solution to precipitate 0.3 g of [Co(TMAP)][BF$_4$]$_5$.6H$_2$O.

|  |  | C | H | N |
|---|---|---|---|---|
| Analysis | % Calc. | 46.47 | 5.02 | 7.75 |
|  | % Found | 46.41 | 4.99 | 8.44 |

EXAMPLE 2

The product of Example 1 and metal complexes of tetra(4-N-methylpyridyl)porphine (TMPyP) and tetraphenylporphinesulfonate (TPPS), were examined for radiosensitizing activity in vitro.

[Co(tetra(4-N-methylpyridyl)porphine) [tosylate]$_5$ (Co(TMPyP)) and Na$_3$[Co(tetraphenylporphinesulfonate)] (Co(TPPS)) were purchased from Porphyrin Products, Logan, Utah.

The results are shown in Table I. Cobalt complexes display activity superior to other metal complexes and thus may be effectively used as radiosensitizers in combination with irradiation.

TABLE I

| Compound | Conc. (mm) | SER (hypoxic V79 cells) | SER (oxic V79 cells) |
|---|---|---|---|
| Co(TMPyP) | 100 | 1.4 | 1.3 |
| TMPyP | 100 | 1.1 | 1.0 |
| Fe(TMPyP) | 100 | 1.3 | 1.0 |
| Cu(TMPyP) | 100 | 1.3 | 1.3 |
| Zn(TMPyP) | 100 | 1.3 | 1.2 |
| Co(TPPS) | 25 | 2.1 | 1.3 |
| TPPS | 100 | 1.2 | 1.0 |
| Fe(TPPS) | 100 | 1.2 | 1.2 |
| Co(TMAP) | 100 | 1.5 | 1.1 |

EXAMPLE 3

Preparation of Co(tetra(4-N-n-butylpyridyl)porphine (metal free version described by V. N. Madakyan, et al, *Arm. Khim. Zh.* 38(6): 391-396 (1985)).

An aqueous solution of 2.38 g CoCl$_2$.2H$_2$O and 0.57 g tetra(4-N-n-butylpyridyl)porphine was refluxed in air for 21 h. A filtered solution of 4g NaBF$_4$ in 30ml H$_2$O was added while the above solution was still hot. This solution was cooled to 5° C. for 24 hours during which time the product precipitated. The product was collected by vacuum filtration. The precipitate was redissolved in acetone/H$_2$O containing a small amount of NaBF$_4$ and placed in an open beaker. As the acetone evaporated, dark purple needles slowly deposited and were collected by vacuum filtration.

Yield: 0.5 g of [Co(tetra(4-N-nbutylpyridyl)porphine)]

Elemental analysis for C$_{56}$H$_{66}$B$_5$CoF$_{20}$N$_8$O$_3$:
Calculation: C 48.32, H 4.78, N 8.05
Found: C 48.11, H 4.87, N 8.08

It will be recognized that various modifications may be made in the invention as described above. Accordingly, the scope of the invention is defined in the following claims wherein:

What is claimed is:

1. A method for rendering hypoxic and oxic cells more sensitive to ionizing irradiation which comprises subjecting the cells to treatment with a radiosensitizing amount of a Co (III) complex of water soluble meso-substititued porphyrins of the general formula (I)

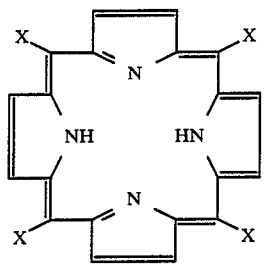
(I)

wherein X is

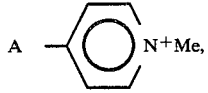   A or the corresponding compound with the N in the 2 or 3 position;

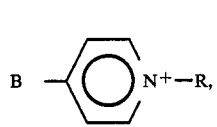   B or the corresponding compound with the N in the 2 or 3 position, where R=a $C_2$–$C_6$ n-alkyl;

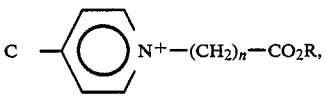   C or the corresponding compound with the N in the 2 or 3 position, where n=1–4 and R=methyl, ethyl or hydrogen;

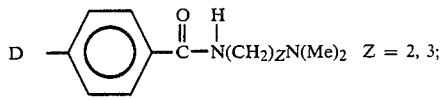   D

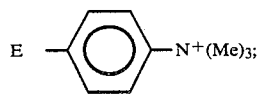   E

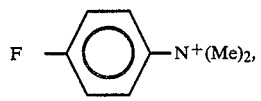   F where R=$C_3$–$C_6$ n-alkyl;

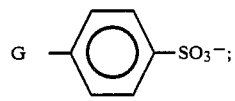   G

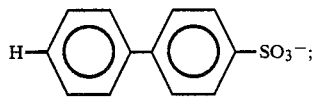   H

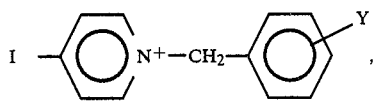   I where Y=H, Cl, Br, or $NO_2$; or

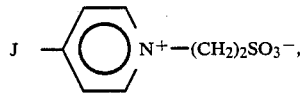   J or the corresponding compound with the N in the 2 or 3 position.

and pharmaceutically acceptable salts thereof.

2. The method of claim 1 wherein the treatment is carried out before irradiation.

3. The method of claim 1 wherein the compound is Co(tetra(4-N-methylpyridyl)porphine); Co(tetraphenylporphinesulfonate); Co(tetra(trimethylaminophenyl)porphine); or Co(tetra(4-N-n-butylpyridyl)porphine).

* * * * *